US011376095B2

(12) United States Patent
 Katsuki

(10) Patent No.: US 11,376,095 B2
(45) Date of Patent: Jul. 5, 2022

(54) MEDICAL DISPLAY DEVICE AND MEDICAL OBSERVATION DEVICE

(71) Applicant: Sony Olympus Medical Solutions Inc., Tokyo (JP)

(72) Inventor: Shinji Katsuki, Tokyo (JP)

(73) Assignee: SONY OLYMPUS MEDICAL SOLUTIONS INC., Tokyo (JP)

( * ) Notice: Subject to any disclaimer, the term of this patent is extended or adjusted under 35 U.S.C. 154(b) by 0 days.

(21) Appl. No.: 16/760,451

(22) PCT Filed: Aug. 29, 2018

(86) PCT No.: PCT/JP2018/031874
§ 371 (c)(1),
(2) Date: Apr. 30, 2020

(87) PCT Pub. No.: WO2019/092954
PCT Pub. Date: May 16, 2019

(65) Prior Publication Data
US 2020/0289235 A1 Sep. 17, 2020

(30) Foreign Application Priority Data
Nov. 7, 2017 (JP) .............................. JP2017-214715

(51) Int. Cl.
*G09G 5/373* (2006.01)
*G09G 5/38* (2006.01)
(Continued)

(52) U.S. Cl.
CPC ............ *A61B 90/37* (2016.02); *A61B 90/361* (2016.02); *G02B 27/0101* (2013.01);
(Continued)

(58) Field of Classification Search
CPC ......... A61B 90/37; A61B 6/481; A61B 6/484; G02B 27/0101; G02F 1/13338; G09G 5/373; G09G 5/38
See application file for complete search history.

(56) References Cited

U.S. PATENT DOCUMENTS 5,526,812 A * 6/1996 Dumoulin .............. G16H 40/63
 600/407
5,694,142 A * 12/1997 Dumoulin .............. G16H 50/50
 345/9
(Continued)

FOREIGN PATENT DOCUMENTS

JP 08-66354 A 3/1996
JP 08-280710 A 10/1996
(Continued)

OTHER PUBLICATIONS

International Search Report and Written Opinion dated Sep. 25, 2018 for PCT/JP2018/031874 filed on Aug. 29, 2018, 10 pages including English Translation of the International Search Report.

*Primary Examiner* — Kevin M Nguyen
(74) *Attorney, Agent, or Firm* — Xsensus LLP

(57) ABSTRACT

A medical display device includes a display device capable of changing the degree of transparency of a display screen, a holding device that holds the display device, and a control device that controls the degree of transparency of the display screen and controls display on the display screen, wherein the display device is held by the holding device so as to be
(Continued)

arranged between an operation part of a patient and a medical worker who performs medical practice for the patient.

20 Claims, 6 Drawing Sheets

(51) Int. Cl.
*A61B 90/00* (2016.01)
*G02B 27/01* (2006.01)
*G02F 1/1333* (2006.01)
*G02F 1/137* (2006.01)
*A61B 5/00* (2006.01)

(52) U.S. Cl.
CPC .......... *G02F 1/137* (2013.01); *G02F 1/13338* (2013.01); *G09G 5/373* (2013.01); *G09G 5/38* (2013.01); *A61B 5/7425* (2013.01); *A61B 2090/372* (2016.02); *A61B 2560/0443* (2013.01); *A61B 2560/0487* (2013.01); *G02B 2027/014* (2013.01); *G02B 2027/0141* (2013.01); *G02F 2203/01* (2013.01); *G09G 2354/00* (2013.01)

(56) References Cited

U.S. PATENT DOCUMENTS

| | | |
|---|---|---|
| 6,847,336 B1 | 1/2005 | Lemelson et al. |
| 2013/0151958 A1* | 6/2013 | Muto .................... G06F 3/0482 715/273 |
| 2017/0007351 A1* | 1/2017 | Yu ........................ A61B 90/30 |
| 2017/0143442 A1* | 5/2017 | Tesar .................... A61B 90/37 |
| 2018/0217429 A1† | 8/2018 | Busch |

FOREIGN PATENT DOCUMENTS

| | | |
|---|---|---|
| JP | 2007-536584 A | 12/2007 |
| JP | 2015-173848 A | 10/2015 |
| JP | 2017-146373 A | 8/2017 |
| WO | 2015/164402 A1 | 10/2015 |

* cited by examiner
† cited by third party

MEDICAL DISPLAY DEVICE AND MEDICAL OBSERVATION DEVICE

CROSS-REFERENCE TO RELATED APPLICATIONS

The present application is based on PCT filing PCT/JP2018/031874, filed Aug. 29, 2018, which claims priority to JP 2017-214715, filed Nov. 7, 2017, the entire contents of each are incorporated herein by reference.

TECHNICAL FIELD

The present disclosure relates to a medical display device and a medical observation device.

BACKGROUND ART

In recent years, in a medical field, there are cases where a medical observation device capable of magnifying an observation object such as an affected part are used in order to support microsurgery such as neurosurgical procedure. Examples of the medical observation device include a medical observation device including an optical microscope and a medical observation device including an imaging device functioning as an electronic imaging-type microscope. Hereinafter, the medical observation device including the optical microscope is referred to as an "optical medical observation device". Hereinafter, the medical observation device including the imaging device is referred to as an "electronic imaging-type medical observation device" or simply a "medical observation device".

With improvement in image quality of the imaging device and improvement in image quality of the display device on which a captured image is displayed, the electronic imaging-type medical observation device can obtain image quality equal to or higher than that of the optical medical observation device. Furthermore, a user (e.g., medical workers such as operators and assistant operators) using an electronic imaging-type medical observation device does not need to look into the eyepiece constituting the optical microscope as in the case of using an optical medical observation device, and therefore the position of the imaging device can be moved more freely. For this reason, use of the electronic imaging-type medical observation device has an advantage that the operation can be supported more flexibly by the movement of the position of the imaging device, and the use of the electronic imaging-type medical observation device in the medical field has been advanced.

Under such a circumstance, a technology related to a display device used in an operation site has been developed. Examples of the above-described technology include the technology described in Patent Literature 1 below.

CITATION LIST

Patent Literature

Patent Literature 1: JP 8-66354 A

DISCLOSURE OF INVENTION

Technical Problem

At the operation site, the display device is arranged, for example, beside the operating table or suspended from the ceiling. On the display device arranged as described above, for example, a captured image that a medical observation device has captured a patient who is to receive medical practice is displayed. An operator such as an operating surgeon or an assistant performs medical practice while viewing the captured image displayed on the display screen of the display device. Hereinafter, a captured image of a patient who is to receive medical practice is referred to as a "captured medical image". In addition, hereinafter, a display device applicable to a medical field, such as a display device on which a captured medical image can be displayed, is referred to as a "medical display device".

However, when the operator performs medical practice while viewing the display screen of the medical display device arranged as described above, there occurs "deviation between the actual direction of an affected part of the patient who receives medical practice viewed from the operator and the direction of the display screen on which the captured medical image of the affected part is displayed viewed from the operator". In addition, even when the display device has a configuration in which the orientation direction of the display device can be adjusted, such as the display device disclosed in Patent Literature 1, a deviation in direction as exemplified above may occur. Then, the deviation in direction as exemplified above may give a great sense of strangeness to a medical doctor or the like who has performed a conventional laparotomy without using any medical observation device. Hereinafter, the deviation in direction as exemplified above is referred to as a "gaze axis difference".

The present disclosure proposes a novel and improved medical display device and a medical observation device that are capable of improving convenience for medical workers.

Solution to Problem

According to the present disclosure, there is provided a medical display device including: a display device capable of changing a degree of transparency of a display screen; a holding device that holds the display device; and a control device that controls the degree of transparency of the display screen and controls display on the display screen, wherein the display device is held by the holding device so as to be arranged between an operation part of a patient and a medical worker who performs medical practice for the patient.

Moreover, according to the present disclosure, there is provided a medical observation device including: a display device capable of changing a degree of transparency of a display screen; an imaging device that captures a captured medical image; a holding device that holds the display device and the imaging device; and a control device that controls the degree of transparency of the display screen and controls display on the display screen, wherein the display device is held by the holding device so as to be arranged between an operation part of a patient and a medical worker who performs medical practice for the patient, and the imaging device captures a captured medical image in which the operation part of the patient is enlarged.

Advantageous Effects of Invention

According to the present disclosure, convenience for medical workers can be improved.

Note that the above effects are not necessarily restrictive, and any of the effects presented in the present description or other effects that can be understood from the present description may be achieved together with or in place of the above effects.

BEST MODE FOR CARRYING OUT THE INVENTION

Figure 1:
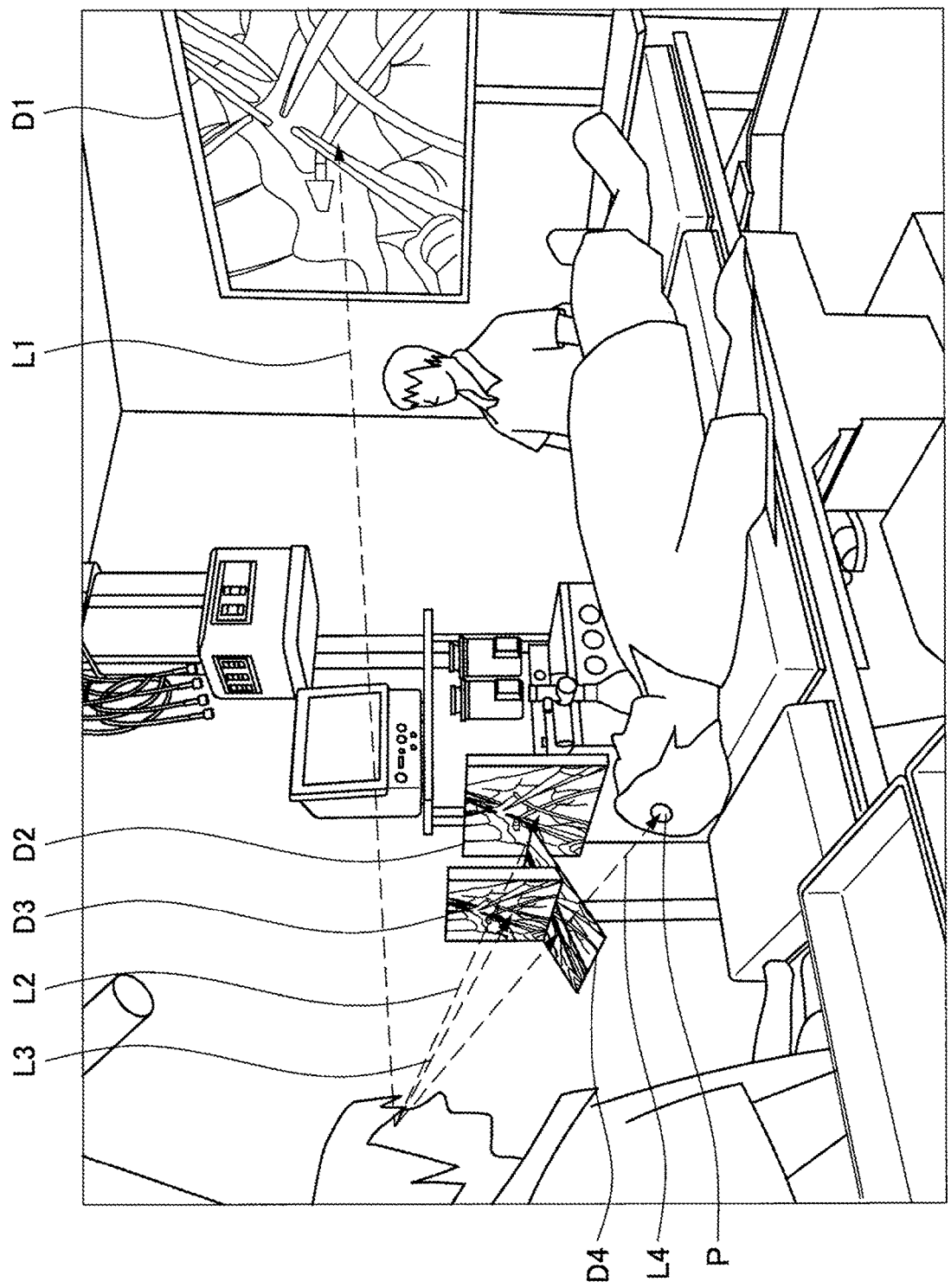
FIG. 1 is an explanatory drawing for explaining an outline of a medical display device according to a present embodiment.

A preferred embodiment of the present disclosure will now be described in detail with reference to the accompanying drawings hereinafter. In the present description and drawings, components having substantially the identical function and configuration are denoted by the same reference numerals, and thus redundant description thereof will be omitted.

Hereinafter, description will be given in the following order.

1. Medical display device according to the present embodiment

[1] Outline of the medical display device according to the present embodiment

[2] Example of the configuration of the medical display device according to the present embodiment

[3] Example of the effects achieved by using the medical display device according to the present embodiment (Medical Display Device According to the Present Embodiment)

[1] Outline of the Medical Display Device According to the Present Embodiment

Prior to an example of the configuration of the medical display device according to the present embodiment, an outline of the medical display device according to the present embodiment will be described.

FIG. 1 is an explanatory drawing for explaining the outline of the medical display device according to the present embodiment. FIG. 1 schematically illustrates an example of the operation site where microsurgery is performed on an affected part P of a patient. The affected part P corresponds to an operation part where an operator performs a procedure.

As described above, in the operation site where the medical observation device is used, the medical display device capable of displaying a captured medical image on the display screen is arranged. FIG. 1 illustrates four medical display devices arranged at four places, i.e., a medical display device D1, a medical display device D2, a medical display device D3, and a medical display device D4, for convenience of description. Needless to say, the arrangement of the medical display devices, the screen size of the medical display devices, and the number of the medical display devices are not limited to the example presented in FIG. 1.

Let gaze directions L1 to L4 be directions of gaze when the operator looks at a certain position on a captured medical image displayed on the display screens of the medical display devices D1 to D4, respectively.

At this time, when the size of the display screen of the medical display device D1 is 55 inches, the gaze axis difference when the operator looks at the display screen of the medical display device D1 is 42.9 [degrees]. When the size of the display screen of the medical display device D2 is 15.6 inches, the gaze axis difference when the operator looks at the display screen of the medical display device D2 is 12.7 [degrees]. When the size of the display screen of the medical display device D3 is 12.5 inches, the gaze axis difference when the operator looks at the display screen of the medical display device D3 is 11.7 [degrees]. As described above, the gaze axis difference may give a great sense of strangeness to a medical doctor or the like who has performed a conventional laparotomy. It is also considered that the larger the gaze axis difference becomes, the greater the sense of strangeness to be given becomes.

On the other hand, the gaze axis difference when the operator looks at the display screen of the medical display device D4 is 0 [degrees]. Hence, as illustrated in the medical display device D4 of FIG. 1, if the medical display device is arranged at a position where the gaze axis difference becomes 0 [degrees], it is possible to eliminate a sense of strangeness caused by the gaze axis difference.

However, as illustrated in the medical display device D4 of FIG. 1, when the medical display device is arranged at a position where the gaze axis difference becomes 0 [degrees], the medical display device blocks the operator's field of vision, and thus it is impossible for the operator to directly look at the affected part of the patient. Accordingly, the convenience of a medical worker such as an operator may not be sufficiently improved simply by arranging the medical display device at a position where the gaze axis difference becomes 0 [degrees].

For this reason, the medical display device according to the present embodiment has a configuration capable of being arranged at a position where the gaze axis difference becomes 0 [degrees], and has a configuration capable of changing the degree of transparency of the display screen.

As described above, it is possible to eliminate a sense of strangeness caused by the gaze axis difference by having a configuration capable of being arranged at a position where the gaze axis difference becomes 0 [degrees]. In addition, it becomes possible for the medical worker such as an operator to directly look at the affected part of the patient through the display screen of the medical display device according to the present embodiment by having a configuration capable of changing the degree of transparency of the display screen.

Accordingly, the medical display device according to the present embodiment can improve the convenience of the medical worker such as an operator by "having a configuration capable of being arranged at a position where the gaze axis difference becomes 0 [degrees], and has a configuration capable of changing the degree of transparency of the display screen".

[2] Example of the Configuration of the Medical Display Device According to the Present Embodiment Next, an example of the configuration of the medical display device according to the present embodiment will be described.

Figure 2:
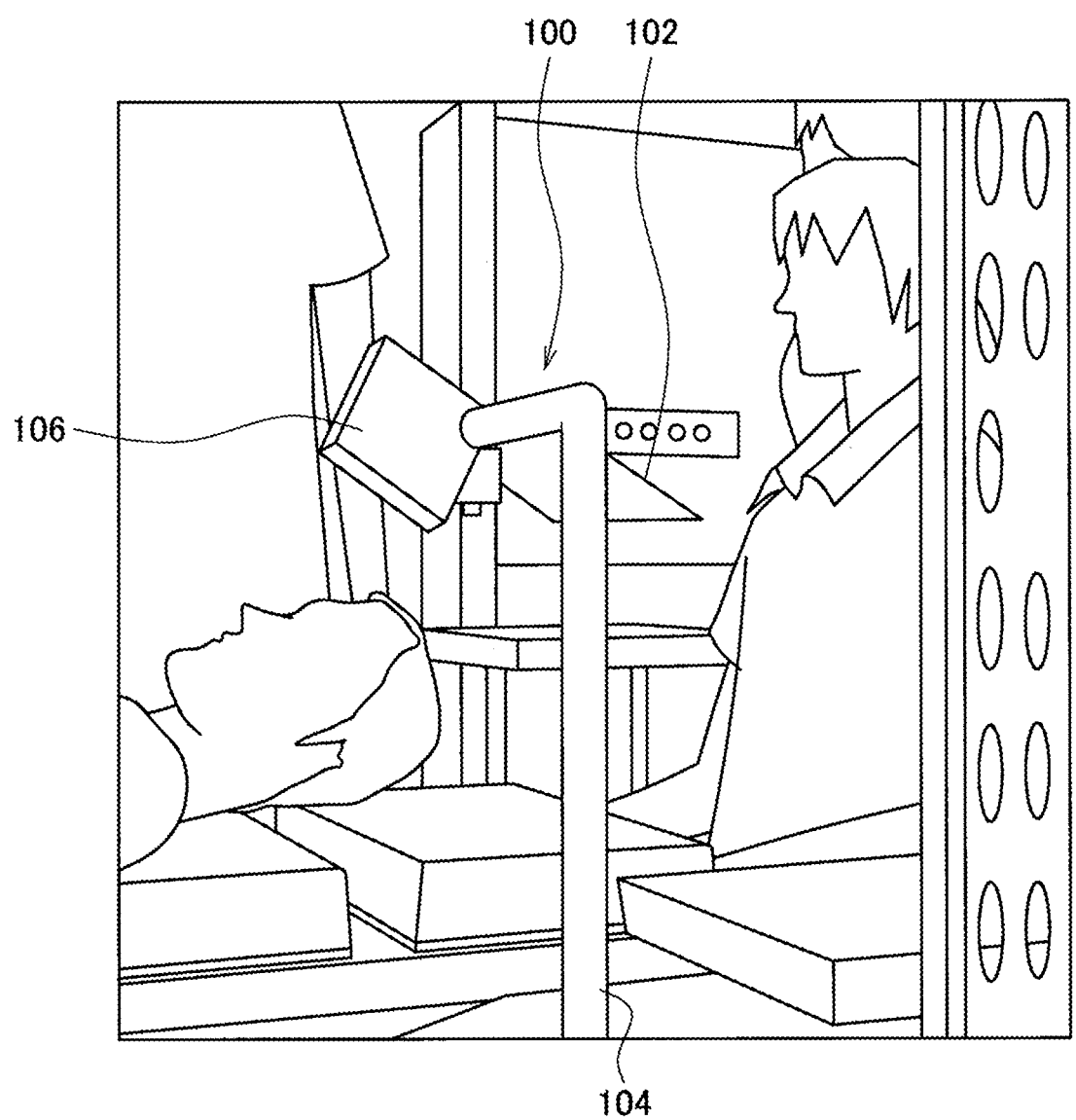
FIG. 2 is an explanatory drawing illustrating a first configuration example of the medical display device according to the present embodiment.
Figure 3A:
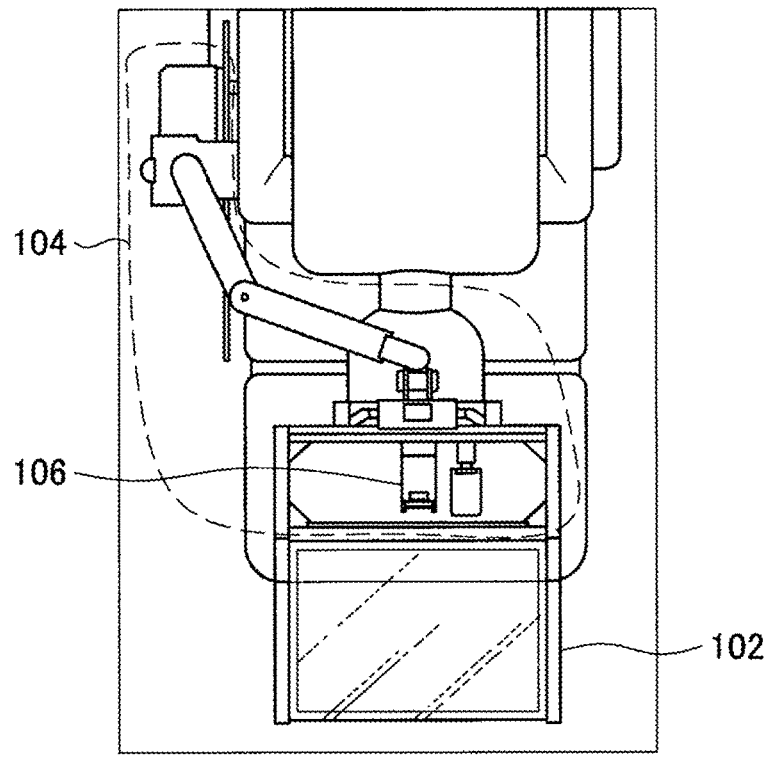
FIG. 3A is an explanatory drawing illustrating a second configuration example of the medical display device according to the present embodiment.
Figure 3B:
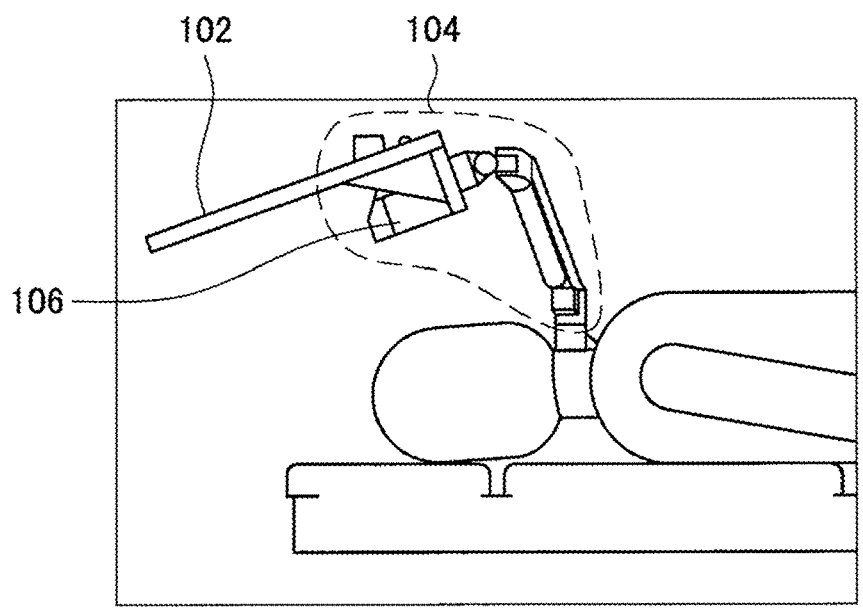
FIG. 3B is an explanatory drawing illustrating the second configuration example of the medical display device according to the present embodiment.
Figure 3C:
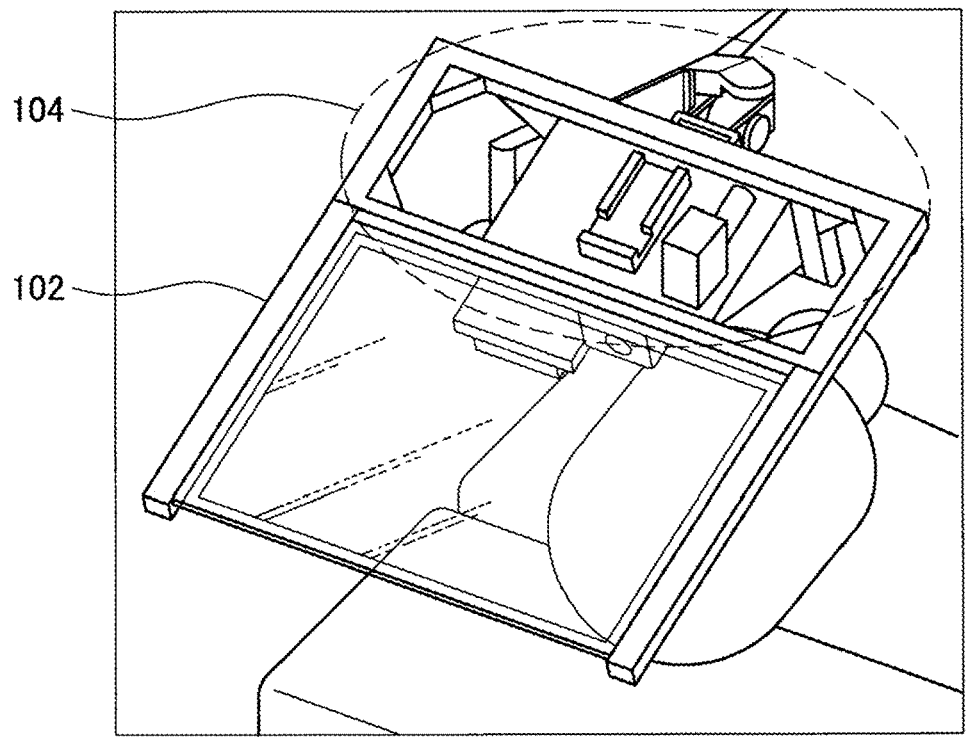
FIG. 3C is an explanatory drawing illustrating the second configuration example of the medical display device according to the present embodiment.
Figure 3D:
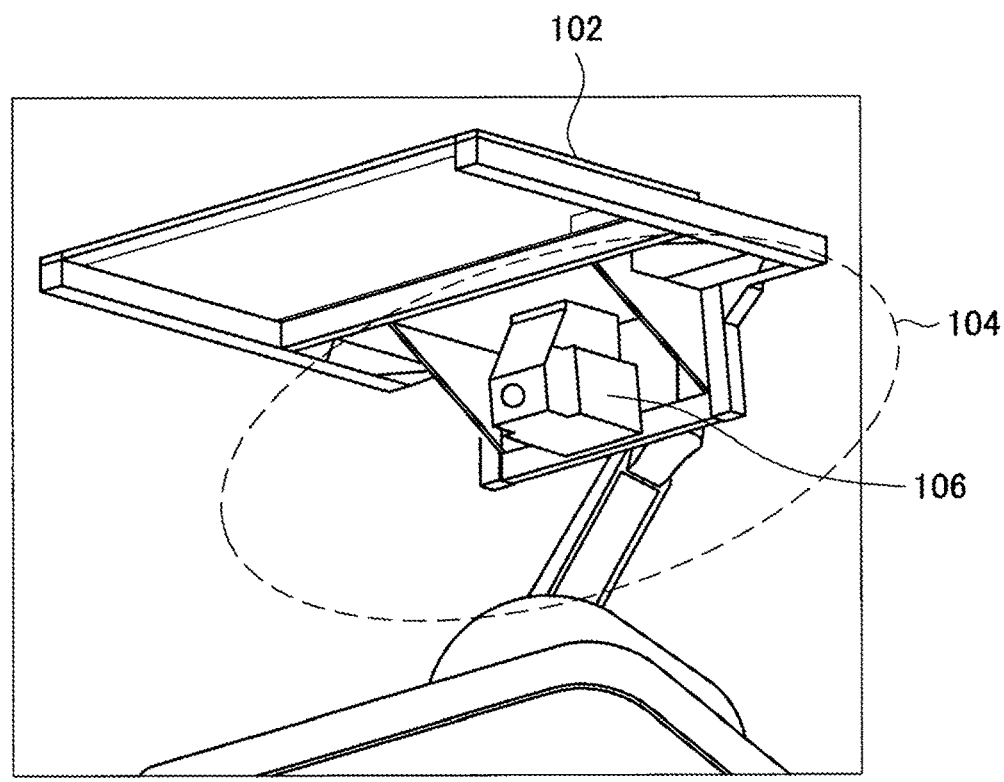
FIG. 3D is an explanatory drawing illustrating the second configuration example of the medical display device according to the present embodiment.

FIG. 2 is an explanatory drawing illustrating the first configuration example of a medical display device 100 according to the present embodiment. FIG. 3A, FIG. 3B, FIG. 3C, and FIG. 3D are explanatory drawings illustrating the second configuration example of the medical display device 100 according to the present embodiment. FIGS. 3A to 3D are views of the medical display device 100 according to the second configuration example viewed from different directions.

The medical display device 100 includes, for example, a display device 102, a holding device 104, and a control device 106.

The medical display device 100 may include one or two or more other components such as a communication device (described later), an imaging device (described later), an operation device (described later), and a storage device (described later), for example. Depending on the configuration of the display device 102 described later, the medical display device 100 may include a projector such as a short focus projector. The medical display device 100 is driven by power supplied from an internal power source such as a battery included therein or power supplied from an external power source connected to the medical display device 100.

Figure 4:
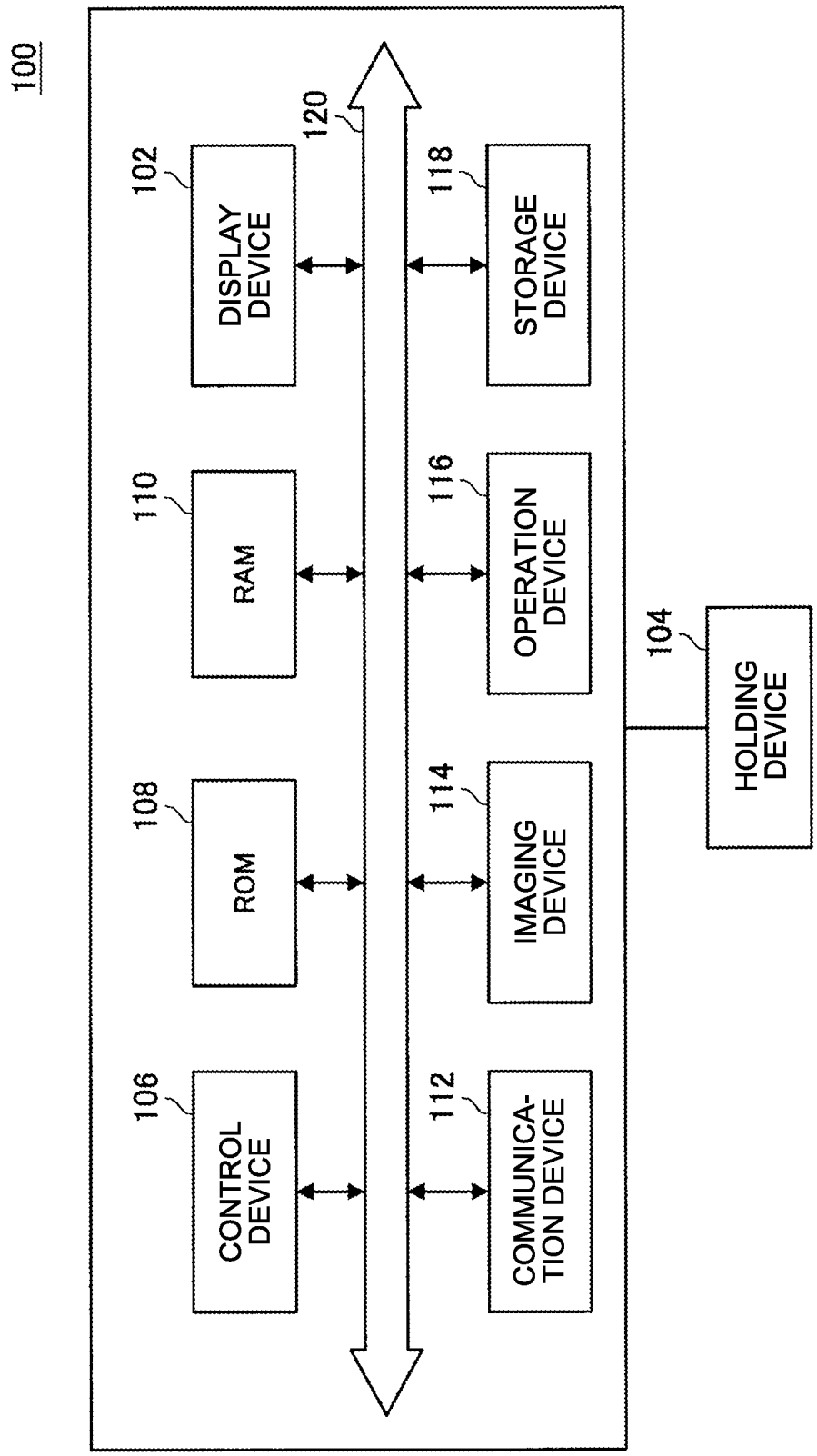
FIG. 4 is a hardware block diagram illustrating an example of a hardware configuration of the medical display device according to the present embodiment.

FIG. 4 is a hardware block diagram illustrating an example of the hardware configuration of the medical display device 100 according to the present embodiment. The medical display device 100 includes, for example, the display device 102, the holding device 104, the control device 106, a ROM (Read Only Memory) 108, a RAM (Random Access Memory) 110, a communication device 112, an imaging device 114, an operation device 116, and a storage device 118. In the medical display device 100, for example, the display device 102, the control device 106, the ROM 108, the RAM 110, the communication device 112, the imaging device 114, the operation device 116, and the storage device 118 are connected to one another via a bus 120 serving as a data transmission path.

The display device 102, the holding device 104, and the control device 106 will each be described later.

The ROM 108 stores control data such as programs and arithmetic parameters used by the control device 106. The RAM 110 temporarily stores, for instance, a program executed by the control device 106 or the like.

The communication device 112 is a communication means included in the medical display device 100, and serves to communicate with an external device of the medical display device 100, such as a medical observation device (not illustrated) or a biological monitor (not illustrated). Examples of the communication device 112 include an IEEE 802.15.1 port and a transmission/reception circuit (wireless communication), an IEEE 802.11 port and a transmission/reception circuit (wireless communication), a communication antenna and a Radio Frequency (RF) circuit (wireless communication), and a Local Area Network (LAN) terminal and a transmission/reception circuit (wired communication). The communication device 112 may have a configuration capable of communicating with one or two or more external devices by a plurality of communication methods.

The medical display device 100 may have a configuration not including the communication device 112. If having a configuration not including the communication device 112, the medical display device 100 is capable of communicating with an external device of the medical display device 100 via an external communication device having been connected.

The imaging device 114 is an imaging means included in the medical display device 100 and generates a captured image (moving image or still image) by capturing an image. The captured image captured by the imaging device 114 is displayed on a display screen of a display device described later, for instance. That is, the medical display device 100 including the imaging device 114 can function as a medical observation device. The medical display device 100 may have a configuration not including the imaging device 114.

The imaging device 114 is configured to include, for example, a lens/imaging element and a signal processing circuit. The lens/imaging element is constituted by, for example, an optical lens and an image sensor using a plurality of imaging elements such as a Complementary Metal Oxide Semiconductor (CMOS) and a Charge Coupled Device (CCD). The signal processing circuit includes, for example, an Automatic Gain Control (AGC) circuit and an Analog to Digital Converter (ADC), and converts an analog signal generated by the imaging element into a digital signal (image data). The signal processing circuit performs various processing related to RAW development, for instance. Furthermore, the signal processing circuit may perform various signal processing such as white balance correction processing, color tone correction processing, gamma correction processing, YCbCr conversion processing, and edge enhancement processing.

The imaging device 114 may have a configuration capable of switching between a plurality of observation modes. The observation modes according to the present embodiment include, for example, an observation mode in which imaging is performed with natural light, an observation mode in which imaging is performed using an image enhancement observation technique such as Narrow Band Imaging (NBI), and an observation mode in which imaging is performed with special light. The special light according to the present embodiment is light in a specific wavelength band, such as light in a near infrared wavelength band or light in a fluorescence wavelength band for fluorescence observation using 5-Aminolevulinic Acid (5-ALA).

Examples of the configuration of the imaging device 114 capable of switching between the plurality of observation modes include a "configuration including a filter that transmits light in a specific wavelength band and does not transmit light in other wavelength bands, and a movement mechanism that selectively arranges the filter on a light path". The specific wavelength bands transmitted by the filter according to the present embodiment include, for example, a near infrared wavelength band (e.g., a wavelength band of about 0.7 [micrometer] to 2.5 [micrometer]), a fluorescence wavelength band by fluorescence observation using 5-ALA (e.g., a wavelength band of about 0.6 [micrometer] to 0.65 [micrometer]), and a fluorescence wavelength band of ICG (Indocyanine Green) (e.g., a wavelength band of about 0.82 [micrometer] to 0.85 [micrometer]).

Note that the imaging device 114 may be provided with a plurality of filters having different transmission wavelength bands. An example in which imaging is performed with light in a specific wavelength band by arranging the filter on the light path has been described above. However, needless to say, the configuration of the imaging device 114 for performing imaging with light in a specific wavelength band is not limited to the example described above.

The operation device 116 is an operation means included in the medical display device 100. By operating the operation device 116, the user of the medical display device 100 can perform some or all of the following operations: designating a predetermined position (described later) on the display screen; changing the degree of transparency of the display screen; and changing the display of the display screen.

Examples of the operation device 116 include a button, a switch, a direction key, and a rotary selector such as a jog dial, or a combination of them.

The medical display device 100 may have a configuration not including the operation device 116. When having a configuration not including the operation device 116, the medical display device 100, based on an operation signal in response to an operation transmitted from an external operation device, performs an action corresponding to the operation.

Examples of the external operation device include devices capable of performing a physical operation such as a foot switch and a remote controller. The external operation device may be a "voice input device such as a microphone" or a "motion sensor such as an acceleration sensor and/or a gyro sensor". That is, the operation signal in response to the operation may include a signal in response to an operation of a given system such as a voice signal in response to a voice operation or an output signal of a motion sensor in response to a motion operation.

The storage device 118 is a storage means included in the medical display device 100. The storage device 118 stores, for example, a "program (computer program) executable by a processor (described later) or the like constituting the control device 106", "various data used for control in the control device 106 such as a first value described later and a second value described later", a "captured medical image", "display data such as data indicating a display object", and the like. Examples of the display object according to the present embodiment include any image such as an icon, a character string, or a combination of them.

Examples of the storage device 118 include a magnetic recording medium such as a hard disk and a nonvolatile memory such as a flash memory. The storage device 118 may also be removable from the medical display device 100.

The medical display device 100 may have a configuration not including the storage device 118. When having a configuration not including the storage device 118, for instance, the control device 106 included in the medical display device 100 can perform various types of controls using data stored in an external storage medium having been connected.

[2-1] Display Device 102

The display device 102 is a display device capable of changing the degree of transparency of the display screen. By changing the degree of transparency of the display screen, the following states are realized in the display device 102. Hereinafter, the display screen of the display device 102 may be simply referred to as the "display screen".

The entire display screen is in a transparent state
The entire display screen is in an opaque state
The entire display screen is in a translucent state
A state in which a part in the transparent state and/or a part in the translucent state are/is included in a part of display screen The transparent state according to the present embodiment refers to, for example, a state in which the transmittance of the display screen is equal to or greater than the first value having been set (alternatively, a state in which the transmittance is greater than the first value). Examples of the first value include, for example, 99 [%] and 80 [%]. The first value corresponding to the transparent state may be a preset fixed value or may be a variable value that can be changed by an operation to the operation device 116 or the like.

The opaque state according to the present embodiment refers to, for example, a state in which the transmittance of the display screen is equal to or smaller than the second value having been set (alternatively, a state in which the transmittance is smaller than the second value). Examples of the second value include, for example, 1 [%] and 10 [%]. The second value corresponding to the opaque state may be a preset fixed value or may be a variable value that can be changed by the operation to the operation device 116 or the like.

The translucent state according to the present embodiment refers to a state that is neither the transparent state nor the opaque state. When the transparent state and the opaque state are controlled by transmittance, for example, a state in which the transmittance of the display screen is larger than the second value and smaller than the first value corresponds to the translucent state.

Examples of the display device 102 include the following ones.

A configuration having a panel using liquid crystal, and changing the degree of transparency of the display screen by applying voltage to the liquid crystal A self-luminous type configuration in which a self-luminous element such as an Organic Light Emitting Diode (OLED) is formed on a transparent glass When the display device 102 is configured to have a panel using liquid crystal, an image is displayed on the display screen of the display device 102 by projection by a projector such as a short focus projector, for example. The display device 102 configured to have a panel using liquid crystal is not limited to the example shown above. For instance, the display device 102 may display an image on the display screen of the display device 102 by causing light of a Light Emitting Diode (LED) to enter from the side surface of the liquid crystal cell. In the display device 102 having a structure in which LED light enters from the side surface of the liquid crystal cell, the degree of transparency of the display screen is changed by switching the presence and absence of scattering of the LED light of entering the liquid crystal cell by application of voltage to the liquid crystal, for example.

Hereinafter, an example will be given in which the display device 102 has a "configuration in which the display device 102 has a panel using liquid crystal, and an image is displayed by projection by a projector such as a short focus projector". The example of the display device 102 is not limited to the example shown above, and may be any type of display device capable of changing the degree of transparency of the display screen.

The display device 102 may also function as a touchscreen.

The display device 102 functions as a touchscreen by having, for example, a configuration corresponding to the mutual capacitance system or a configuration corresponding to the self capacitance system. The display device 102 may have a sensor capable of detecting movement such as an infrared sensor, and may also function as a touchscreen by detecting movement by the sensor.

[2-2] Holding Device 104

The holding device 104 is a device that holds the display device 102.

For example, as illustrated in FIGS. 2 and 3A to 3D, the display device 102 is held by the holding device 104 so as to be arranged between the patient and the medical worker who performs medical practice for the patient. By being arranged between the patient and the medical worker, the display device 102 has a barrier function that protects the medical worker from scattering of blood or the like when sudden hemorrhage or the like occurs during the operation. Accordingly, the display device 102 is arranged by the holding device 104 between the patient and the medical worker, thereby enhancing the safety of the medical worker such as the operator.

Examples of the holding device 104 include, as illustrated in FIG. 2, an arm holding the display device 102 so as to fix its position. The arm is attached to, for example, a bed on which the patient receiving the medical practice lies.

The holding device 104 may also be an arm composed of a plurality of links connected together by joint parts, for example, as illustrated in FIGS. 3A to 3D. When the holding device 104 is an arm composed of the plurality of links connected together by the joint parts, the display device 102 can be held while giving a degree of freedom to the position of the display device 102. The degree of freedom of the position of the display device 102 can be set to have a desired degree of freedom by, for example, the number and arrangement of the joint parts and links, the direction of the driving shaft of the joint parts, and the like.

The holding device 104 may also has a mechanism by which, for example, the user of the medical display device 100 can remove the display device 102 from the holding device 104 by performing a predetermined operation. Mechanisms by which the display device 102 can be removed from the holding device 104 include, for example, any mechanisms by which the display device 102 can be removed from the holding device 104, such as a latching removal mechanism, a button removal mechanism, and a thumb-turn removal mechanism. When the holding device 104 has the above mechanism, the holding device 104 removably holds the display device 102. The holding device 104 removably holds the display device 102, thereby making the display device 102 replaceable.

[2-3] Control Device 106

The control device 106 controls the degree of transparency of the display screen and controls display on the display screen.

Examples of the control device 106 include one or two or more processors configured by an arithmetic circuit such as a Micro Processing Unit (MPU). The processor functioning as the control device 106 may also be provided in another component such as a projector or the display device 102. FIGS. 2 and 3A to 3D illustrate an example in which the projector is provided with a processor that functions as the control device 106. The position at which the processor is provided in the projector is not limited to the example presented in FIGS. 2 and 3A to 3D. For example, when the display device 102 is composed of a reflective screen, the projector is provided on the display surface side (side on which the medical worker or the like views the display screen) of the display device 102.

The control device 106 automatically controls the degree of transparency of the display screen and controls display on the display screen by executing a program stored in the storage device 118, for instance.

By way of example, the control device 106 controls display on the display screen in conjunction with control of the degree of transparency of the display screen. Examples of the control of the display on the display screen in conjunction with the control of the degree of transparency of the display screen include the following. Needless to say, the example of the control of the display on the display screen in conjunction with the control of the degree of transparency of the display screen is not limited to the following example. A display example realized by the control of the display on the display screen in conjunction with the control of the degree of transparency of the display screen will be described later.

When the entire or part of the display screen is in the opaque state, display of the captured medical image, display related to the patient (described later), and the like are performed in the region of the opaque state.

When the entire or part of the display screen is in the translucent state, display of the captured medical image and the like are performed in the region of the translucent state.

When the entire or part of the display screen is in the transparent state, nothing is displayed on the region in the transparent state.

When the entire or part of the display screen is in the transparent state, display of the captured medical image, display of the display object, and the like are performed in the region of the transparent state.

The display related to the patient according to the present embodiment includes any display content relating to the patient such as display of vital signs of the patient, display of annotation, display of navigation, display of a captured medical image obtained by special light observation, and display of an enlarged captured medical image (or a reduced captured medical image).

Furthermore, based on the operation to the operation device 116 described above or the operation to the external operation device described above, the control device 106 may perform the control of the degree of transparency of the display screen and/or the control of the display on the display screen.

For example, when the user instructs to change the degree of transparency of the display screen by performing an operation to the operation device 116 or the like, the medical display device 100 changes the degree of transparency of the display screen in response to the operation. Furthermore, for example, when the user instructs to change the display content by performing an operation to the operation device 116 or the like, the medical display device 100 changes the display content displayed on the display screen to the display content corresponding to the operation. Note that the user can also instruct to change the degree of transparency of the display screen and to change the display content by performing an operation to the operation device 116 or the like. That is, the control device 106 can switch the degree of transparency of the display screen and/or the display content in response to the operation to the operation device 116.

As described above, the control device 106 can control the display on the display screen in conjunction with the control of the degree of transparency of the display screen. Thus, for example, when the user instructs to change the degree of transparency of the display screen by performing an operation to the operation device 116 or the like, the control device 106 can change the degree of transparency of the display screen in response to the operation, and can also automatically change the display content in conjunction with the degree of transparency of the display screen.

Hereinafter, an example of the control of the degree of transparency of the display screen in the control device 106 and an example of the control of the display on the display screen in the control device 106 will be described.

[2-3-1] First Example of Control of Degree of Transparency of Display Screen and Control of Display on Display Screen: Example of Control for Entire Display Screen The control device 106 controls the degree of transparency of the entire display screen. More specifically, the control device 106 controls the degree of transparency of the display screen such that the entire display screen is in the transparent state, the entire display screen is in the translucent state, or the entire display screen is in the opaque state.

For example, when the display device 102 is configured to have a panel using liquid crystal, the control device 106 controls the degree of transparency of the entire display screen by applying the identical voltage corresponding to the degree of transparency to the entire display screen of the display device 102.

When the degree of transparency of the display screen is controlled so that the entire display screen is in the transparent state, the control device 106 displays nothing on the display screen, for example. When the degree of transparency of the display screen is controlled so that the entire display screen is in the transparent state, the control device 106 may display the display object on the display screen. An Augmented Reality (AR) display is realized by displaying the display object when the entire display screen is in the transparent state, for example. When the degree of transparency of the display screen is controlled so that the entire display screen is in the transparent state, the control device 106 can also perform the display related to the patient.

When the degree of transparency of the display screen is controlled so that the entire display screen is in the translucent state or the opaque state, the control device 106 displays, for example, the captured medical image and/or the display object on the display screen. When the degree of transparency of the display screen is controlled so that the entire display screen is in the translucent state or the opaque state, the control device 106 may also perform display related to the patient. When the degree of transparency of the display screen is controlled so that the entire display screen is in the translucent state, the control device 106 may display nothing on the display screen.

Needless to say, the example of control of display on the display screen when the degree of transparency is controlled for the entire display screen is not limited to the example presented above.

[2-3-2] Second Example of Control of Degree of Transparency of Display Screen and Control of Display on Display Screen: Example of Control for Each Region Having been Set on Display Screen The control device 106 sets a plurality of regions for the display screen, and controls the degree of transparency of the display screen for each region having been set.

For example, when the display device 102 is configured to have a panel using liquid crystal, the control device 106 controls the degree of transparency for each region having been set, by applying a voltage corresponding to the degree of transparency for each region having been set to the display screen of the display device 102.

Examples of the region set by the control device 106 include the following first to third examples described below.

(1) First Example of Region to be Set

The control device 106 sets a first region including at least a predetermined position of the display screen in the region.

Examples of the predetermined position of the display screen according to the present embodiment include the position of the display screen having been preset such as the center position of the display screen. Furthermore, the predetermined position of the display screen may be a position of the display screen set based on an operation to the operation device 116 included or an operation to an external operation device.

The first region may be a region having a fixed size and shape, or may be a region having a variable size and/or shape based on an operation to the operation device 116 or the like.

The control device 106 controls the degree of transparency of the display screen, for example, such that the first region having been set is in the transparent state or such that the first region having been set is in the translucent state. That is, the first region set by the control device 106 is a region in which the viewer of the display screen can view the other side of the display device 102 through the display screen.

The control device 106 display nothing on the first region, for example. The control device 106 may display, for example, the display object on the first region. For example, an AR display is realized by displaying the display object on the first region. Needless to say, the example of the display on the first region is not limited to the example presented above.

(2) Second Example of Region to be Set

The control device 106 further sets one or two or more second regions on the display screen in a region other than the first region.

The control device 106 sets the second region having any size and shape at any position of the region other than the first region. The position, size, and shape in which the second region can be set may be predetermined in a program stored in the storage device 118. In addition, part or all of the position, size, and shape of the second region may be changeable based on an operation to the operation device 116 or the like.

The control device 106 controls the degree of transparency of the display screen, for example, such that the second region having been set is in the opaque state.

The control device 106 performs, for example, a display related to the patient on the second region. The display performed on the second region is not limited to the display related to the patient, and the control device 106 may display any display content on the second region.

That is, the second region set by the control device 106 can function as a region for displaying a display content capable of assisting the operator performing medical practice, for example.

Note that the control device 106 can also control the degree of transparency of the display screen, for example, such that part or entirety of the second region having been set is in the translucent state or such that part or entirety of the second region having been set is in the transparent state.

(3) Third Example of Region to be Set

The control device 106 controls the degree of transparency of the display screen, for example, such that a region other than the first region and the second region is in the transparent state. The control device 106 display nothing on the other region described above, for example.

Note that the control device 106 may also control the degree of transparency of the display screen such that the other region is in the translucent state or the other region is in the opaque state. Furthermore, the control device 106 may also perform some display on the other region described above, for example.

Examples of the region set by the control device 106 include part or entirety of the region presented in the first example to the region presented in the third example, for instance. Needless to say, the example of the region set by the control device 106 is not limited to the example presented above.

[2-3-3] Display Example on Display Screen

Figure 5:
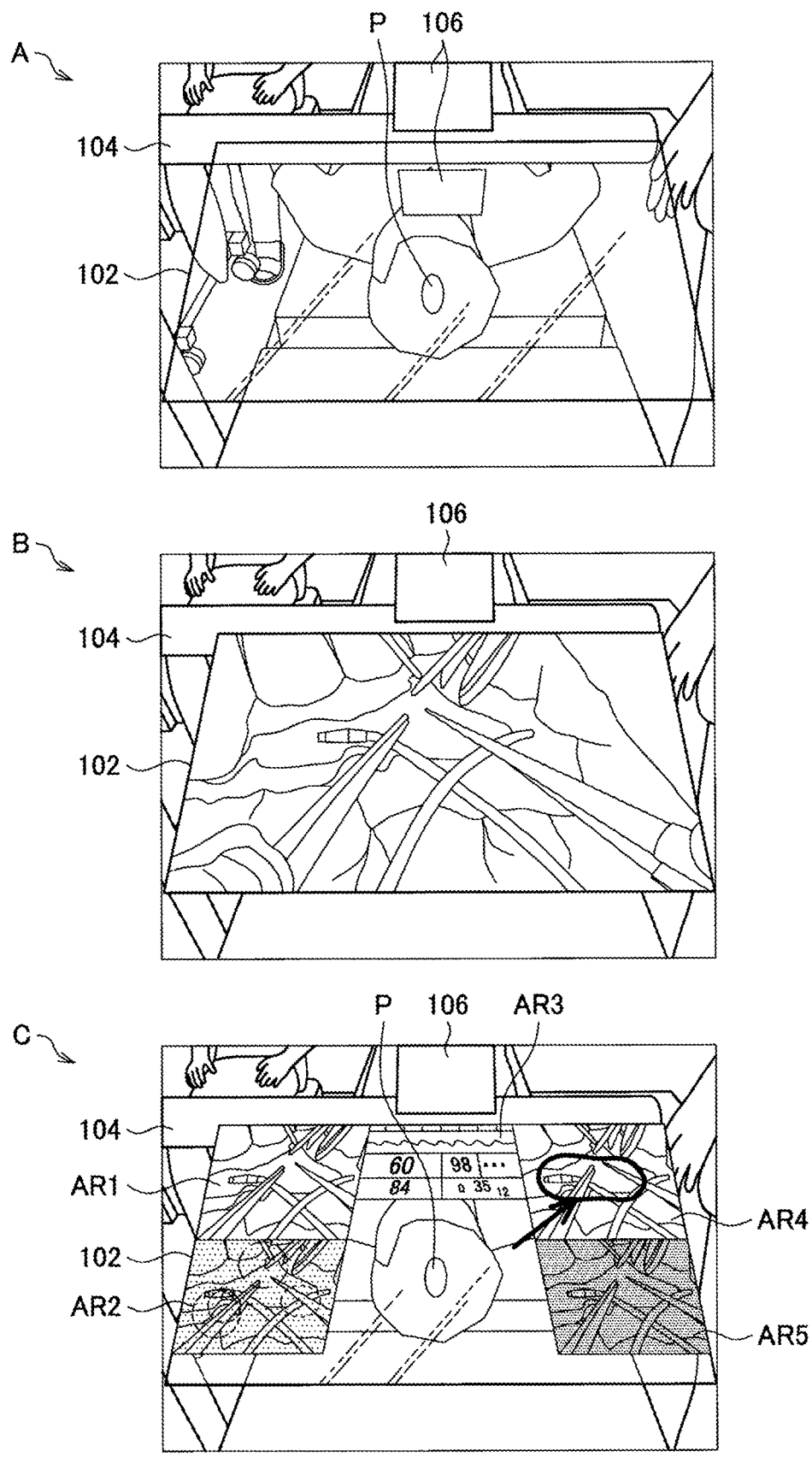
FIG. 5 is explanatory drawings illustrating an example of display realized by control by a control device included in the medical display device according to the present embodiment.

FIG. 5 is explanatory drawings illustrating an example of display realized by control by the control device 106 included in the medical display device 100 according to the present embodiment. A of FIG. 5 illustrates an example of display when the control device 106 performs control for the entire display screen, and illustrates an example of display when the entire display screen is in the transparent state. B of FIG. 5 illustrates another example of display when the control device 106 performs control for the entire display screen, and illustrates an example of display when the entire display screen is in the opaque state. C of FIG. 5 illustrates an example of display when the control device 106 performs control for each region having been set on the display screen. Each region AR1 to AR5 illustrated in C of FIG. 5 corresponds to the second region.

When the entire display screen is made into the transparent state, as illustrated in A of FIG. 5 for example, the affected part P (which corresponds to the operation part) of the patient is visible through the display screen. When the entire display screen is in the transparent state, the transparency is high and the display screen has no distortion, and hence the appearance of the affected part P through the display screen from the operator is almost the same as the direct view of the affected part P. The presence of the display device 102 between the operator and the patient causes, as described above, the display device 102 to have the barrier function from scattering, thereby ensuring the safety of the operator.

When the entire display screen is made into the opaque state, as illustrated in B of FIG. 5 for example, an enlarged captured medical image is displayed on the display screen. A display example when the entire display screen is made into the opaque state is not limited to the example illustrated in B of FIG. 5. For example, when the entire display screen is made into the opaque state, a full-sized captured medical image may be displayed on the display screen, and a display object related to navigation, information related to special light observation, and the like may be superimposed and displayed in an AR manner. The control device 106 may perform time-division control of display and perform 3D display by cooperating with an external device related to 3D display such as shutter glasses.

Furthermore, as described above, the control device 106 can make the entire display screen in the translucent state. When the entire display screen is made into the translucent state, the control device 106 may display a captured medical image such as a captured medical image captured by special light observation so as to overlap the affected part P. By specifying a positional relationship between the display screen and the affected part P based on the captured medical image captured by the imaging device 114, for instance, the control device 106 realizes a display in which the captured medical image is superimposed on the affected part P. At this time, the control device 106 may perform 3D display in cooperation with an external device related to 3D display such as shutter glasses.

When performing control for each region having been set on the display screen, as illustrated in C of FIG. 5 for example, the first region including the affected part P is made into the transparent state, and display related to the patient is performed on the second regions AR1 to AR5. C of FIG. 5 illustrates an example in which display of an enlarged captured medical image, display of navigation, display of vital signs of the patient, display of annotation, and display of a captured medical image obtained by special light observation are performed in order for each of the second regions AR1 to AR5.

Although not explicitly illustrated in C of FIG. 5, the first region is a region other than the second regions AR1 to AR5 and a region including the affected part P. For example, a region other than the second regions AR1 to AR5 in C of FIG. 5 corresponds to an example of the first region. In the example illustrated in C of FIG. 5, another region other than the first region and the second regions AR1 to AR5 may be present. When the other region described above is present, the other region described above is controlled so as to be in the transparent state.

The display illustrated with reference to FIG. 5, for instance, is realized by the control by the control device 106. Needless to say, the display example realized by the control by the control device 106 is not limited to the example illustrated with reference to FIG. 5.

The medical display device 100 has the configuration illustrated with reference to FIGS. 2 and 3A to 3D, for example. Needless to say, the configuration and appearance of the medical display device 100 are not limited to those illustrated with reference to FIGS. 2 and 3A to 3D.

[3] Example of the Effects Achieved by Using the Medical Display Device According to the Present Embodiment By using the medical display device according to the present embodiment, for example, the following effects can be achieved. Needless to say, the effects achieved by using the medical display device according to the present embodiment are not limited to the following examples.

- The medical display device according to the present embodiment has a configuration capable of being arranged at a position where the gaze axis difference becomes 0 [degrees] and capable of changing the degree of transparency of the display screen. Accordingly, by using the medical display device according to the present embodiment, the operator can perform a laparotomy using the medical observation device with his gaze being directed to the affected part (operation part) of the patient.
- By being arranged between the patient and the operator, the display device 102 has the barrier function from scattering, thereby ensuring the safety of the operator.
- By having a configuration in which the display device 102 is replaceable, the display device 102 can be made disposable, resulting in securing the cleanliness of the clean area.
- The display device 102 functioning as a touchscreen allows, for example, the operator to operate the display device by himself, and good operability to be provided to the operator (an example of medical workers).
- It is possible to perform various displays such as displaying a display object related to navigation, information related to special light observation, and the like on the display screen of the display device 102 in an AR manner.

While the preferred embodiment of the present disclosure has been described in detail with reference to the accompanying drawings, the technical scope of the present disclosure is not limited to such examples. It is obvious that a person ordinarily skilled in the art of the present disclosure can conceive of various changes or modifications within the scope of the technical idea described in the claims, which are also understood to naturally fall within the technical scope of the present disclosure.

In addition, the effects described in the present description are only illustrative or exemplary and not restrictive. That is, the technology according to the present disclosure can achieve other effects that are apparent to those skilled in the art from the description of the present description, in addition to or in place of the above effects.

The following configurations also fall within the technical scope of the present disclosure.

(1)

A medical display device including:

a display device capable of changing a degree of transparency of a display screen;

a holding device that holds the display device; and a control device that controls the degree of transparency of the display screen and controls display on the display screen.

(2)

The medical display device according to (1), wherein the display device is held by the holding device so as to be arranged between an operation part of a patient and a medical worker who performs medical practice for the patient.

(3)

The medical display device according to (1) or (2), wherein the control device controls the degree of transparency of the display screen such that the entire display screen is in a transparent state, such that the entire display screen is in a translucent state, or such that the entire display screen is in an opaque state.

(4)

The medical display device according to (1) or (2), wherein the control device sets a plurality of regions for the display screen, and controls the degree of transparency of the display screen for each of the regions having been set.

(5)

The medical display device according to (4), wherein the control device sets a first region including at least a predetermined position of the display screen in the region, and controls the degree of transparency of the display screen such that the first region having been set is in a transparent state or such that the first region having been set is in a translucent state.

(6)

The medical display device according to (5), wherein the predetermined position is a position of the display screen set in the advance.

(7)

The medical display device according to (5), wherein the predetermined position is a position of the display screen set based on an operation of an operation device included in the medical display device or an operation of an external operation device.

(8)

The medical display device according to any one of (5) to (7), wherein the control device sets one or two or more second regions on the display screen in a region other than the first region, and controls the degree of transparency of the display screen such that the second region having been set is in an opaque state.

(9)

The medical display device according to (8), wherein the control device controls display on the display screen such that display related to the patient is performed on the second region.

(10)

The medical display device according to (8) or (9), wherein the control device controls the degree of transparency of the display screen such that a region other than the first region and the second region is in a transparent state.

(11)

The medical display device according to any one of (5) to (10), wherein the control device controls display on the display screen such that a display object is displayed on the first region.

(12)

The medical display device according to any one of (1) to (11), wherein the control device controls the degree of transparency of the display screen and/or controls display on the display screen based on an operation of an operation device included in the medical display device or an operation of an external operation device.

(13)

The medical display device according to any one of (1) to (12), wherein the control device controls display on the display screen in conjunction with control of the degree of transparency of the display screen.

(14)

The medical display device according to any one of (1) to (13), wherein the holding device removably holds the display device, and the display device is replaceable.

(15)

The medical display device according to any one of (1) to (14) wherein the display device functions as a touchscreen.

(16)

The medical display device according to any one of (1) to (15), wherein the holding device has an arm.

(17)

The medical display device according to (16), wherein the arm is composed of a plurality of links connected together by joint parts.

Moreover, the following configurations also fall within the technical scope of the present disclosure.

(1)

A medical display device including:

a display device capable of changing a degree of transparency of a display screen;

a holding device that holds the display device; and a control device that controls the degree of transparency of the display screen and controls display on the display screen, wherein the display device is held by the holding device so as to be arranged between an operation part of a patient and a medical worker who performs medical practice for the patient.

(2)

The medical display device according to (1), wherein the control device controls the degree of transparency of the display screen such that the entire display screen is in a transparent state, such that the entire display screen is in a translucent state, or such that the entire display screen is in an opaque state.

(3)

The medical display device according to (1), wherein the control device sets a plurality of regions for the display screen, and controls the degree of transparency of the display screen for each of the regions having been set.

(4)

The medical display device according to (3), wherein the control device sets a first region including at least a predetermined position of the display screen in the region, and controls the degree of transparency of the display screen such that the first region having been set is in a transparent state or such that the first region having been set is in a translucent state.

(5)

The medical display device according to (4), wherein the control device sets one or two or more second regions on the display screen in a region other than the first region, and controls the degree of transparency of the display screen such that the second region having been set is in an opaque state.

(6)

The medical display device according to (5), wherein the control device controls display on the display screen such that display related to the patient is performed on the second region.

(7)

The medical display device according to (5) or (6), wherein the control device displays an enlarged captured medical image on the second region.

(8)

The medical display device according to any one of (5) to (7), wherein the control device displays, on the second region, an enlarged captured medical image and a display object related to navigation.

(9)

The medical display device according to any one of (5) to (8), wherein the control device displays a vital sign of the patient on the second region.

(10)

The medical display device according to any one of (5) to (9), wherein the control device displays, on the second region, an enlarged captured medical image and a display object related to annotation.

(11)

The medical display device according to any one of (5) to (10), wherein the control device displays, on the second region, a captured medical image obtained by special light observation.

(12)

The medical display device according to any one of (5) to (11), wherein the control device controls the degree of transparency of the display screen such that a region other than the first region and the second region is in a transparent state.

(13)

The medical display device according to any one of (4) to (12), wherein the control device controls display on the display screen such that a display object is displayed on the first region.

(14)

The medical display device according to any one of (1) to (13), wherein the control device controls the degree of transparency of the display screen and/or controls display on the display screen based on an operation of an operation device included in the medical display device or an operation of an external operation device.

(15)

The medical display device according to any one of (1) to (14), wherein the control device controls display on the display screen in conjunction with control of the degree of transparency of the display screen.

(16)

The medical display device according to any one of (1) to (15), wherein the holding device removably holds the display device, and the display device is replaceable.

(17)

The medical display device according to any one of (1) to (16), wherein the display device functions as a touchscreen.

(18)

The medical display device according to any one of (1) to (17), wherein the holding device has an arm.

(19)

The medical display device according to (18), wherein the arm is composed of a plurality of links connected together by joint parts.

(20)

A medical observation device including:

a display device capable of changing a degree of transparency of a display screen;

an imaging device that captures a captured medical image;

a holding device that holds the display device and the imaging device; and a control device that controls the degree of transparency of the display screen and controls display on the display screen, wherein the display device is held by the holding device so as to be arranged between an operation part of a patient and a medical worker who performs medical practice for the patient, and the imaging device captures a captured medical image in which the operation part of the patient is enlarged.

REFERENCE SIGNS LIST

100, D1, D2, D3, D4 MEDICAL DISPLAY DEVICE
102 DISPLAY DEVICE
104 HOLDING DEVICE
106 CONTROL DEVICE
108 ROM
110 RAM
112 COMMUNICATION DEVICE
114 IMAGING DEVICE
116 OPERATION DEVICE
118 STORAGE DEVICE
120 BUS
AR1, AR2, AR3, AR4, AR5 SECOND REGION
L1, L2, L3, L4 GAZE DIRECTION
P AFFECTED PART

The invention claimed is:

1. A medical display system, comprising:
a display capable of changing a degree of transparency of a display screen;
a mount that holds the display; and
control circuitry configured to, on condition that a degree of transparency of an entirety of the display is set to less than a first value and greater than a second value, set a plurality of regions for the display screen, to display different content in at least three regions of the plurality of regions, and to control the degree of transparency of the display screen for each of the plurality of regions, wherein the mount holds the display between an operation part of a patient and a medical worker who performs medical practice for the patient, and the at least three regions include
- a viewing region in which nothing is displayed such that a direct view of the operation part of the patient is unobstructed,
- a detail region in which an enlarged captured medical image of the operation part of the patient is displayed, and
- a supplement region in which one of a supplemental captured medical image, different from the enlarged captured medical image, of the operation part of the patient or vital signs of the patient is displayed.

2. The medical display system according to claim 1, wherein the control circuitry is configured to control the degree of transparency of the display screen such that the entire display screen transparent or is opaque.

3. The medical display system according to claim 1, wherein the control circuitry is configured to control the degree of transparency of the display screen for each of the plurality of regions.

4. The medical display system according to claim 3, wherein
the control circuitry configured to
control the degree of transparency of the display screen such that the viewing region is transparent or translucent.

5. The medical display system according to claim 4, wherein
the control circuitry is configured to:
control the degree of transparency of the display screen such that the detail region and the supplement region are opaque.

6. The medical display system according to claim 4, wherein the control circuitry is configured to control display on the display screen such that a display object is displayed on the viewing region.

7. The medical display system according to claim 1, wherein the control circuitry is configured to control display on the display screen such that display related to the patient is on the supplement region.

8. The medical display system according to claim 1, wherein the control circuitry is configured to display, on the supplement region, the enlarged captured medical image and a display object related to navigation.

9. The medical display system according to claim 1, wherein the control circuitry is configured to display a vital sign of the patient on the supplement region.

10. The medical display system according to claim 1, wherein the control circuitry is configured to display, on the supplement region, the enlarged captured medical image and a display object related to annotation.

11. The medical display system according to claim 1, wherein the control circuitry is configured to display, on the supplement region, a captured medical image obtained by special light observation.

12. The medical display system according to claim 1 wherein the control circuitry is configured to control the degree of transparency of the display screen such that a region other than the viewing region, the detail region, and the supplement region is transparent.

13. The medical display system according to claim 1, wherein the control circuitry is configured to control the degree of transparency of the display screen and/or display on the display screen based on an operation of an operation device included in the medical display system or an operation of an external operation device.

14. The medical display system according to claim 1, wherein
the mount removably holds the display, and
the display is replaceable.

15. The medical display system according to claim 1, wherein the display includes a touchscreen.

16. The medical display system according to claim 1, wherein the mount includes an arm.

17. The medical display system according to claim 16, wherein the arm is composed of a plurality of links connected together by joint parts.

18. The medical display system according to claim 1, wherein the control circuitry is configured to display, on the supplement region, a reduced captured medical image.

19. A medical observation system, comprising:
a display capable of changing a degree of transparency of a display screen;
an image sensor that captures a captured medical image;
a mount that holds display and the image sensor;
control circuitry configured to, on condition that a degree of transparency of an entirety of the display is set to less than a first value and greater than a second value, set a plurality of regions for the display screen, to display different content in at least three regions of the plurality of regions, and to control the degree of transparency of the display screen for each of the plurality of regions, wherein
the mount holds the display between an operation part of a patient and a medical worker who performs medical practice for the patient,
the image sensor outputs an enlarged captured medical image of the operation part of the patient, and
the at least three regions include
- a viewing region in which nothing is displayed such that a direct view of the operation part of the patient is unobstructed,
- a detail region in which the enlarged captured medical image of the operation part of the patient is displayed, and
- a supplement region in which one of a supplemental captured medical image, different from the enlarged captured medical image, of the operation part of the patient or vital signs of the patient is displayed.

20. The medical observation system according to claim 19, wherein the control circuitry is configured to display, on the supplement region, the enlarged captured medical image including a display object related to navigation, the enlarged captured medical image including a display object related to annotation one of a vital sign of the patient, a reduced captured medical image.

* * * * *